US012718946B2

(12) United States Patent
Helm et al.

(10) Patent No.: US 12,718,946 B2
(45) Date of Patent: Aug. 25, 2026

(54) EFFICIENT IDENTIFICATION OF EPILEPTIFORM DISCHARGES IN BRAIN SCAN DATA

(71) Applicant: MICROSOFT TECHNOLOGY LICENSING, LLC, Redmond, WA (US)

(72) Inventors: Hayden Helm, San Francisco, CA (US); Weiwei Yang, Seattle, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 573 days.

(21) Appl. No.: 18/338,169

(22) Filed: Jun. 20, 2023

(65) Prior Publication Data

US 2024/0428938 A1 Dec. 26, 2024

(51) Int. Cl.
*G16H 50/20* (2018.01)
*A61B 5/00* (2006.01)
(Continued)

(52) U.S. Cl.
CPC ........... *G16H 50/20* (2018.01); *A61B 5/4064* (2013.01); *A61B 5/4094* (2013.01); *G06N 3/045* (2023.01); *G06N 3/09* (2023.01); *G16H 50/50* (2018.01)

(58) Field of Classification Search
CPC ...... G16H 50/20; G16H 50/50; A61B 5/4064; A61B 5/4094; A61B 5/369; A61B 5/7267; G06N 3/045; G06N 3/09
See application file for complete search history.

(56) References Cited

U.S. PATENT DOCUMENTS

2022/0022800 A1* 1/2022 Abrams ................. A61B 5/372
2022/0122250 A1* 4/2022 Besson ................ G06N 3/0464

FOREIGN PATENT DOCUMENTS

CN 112842358 A * 5/2021 ........... A61B 5/4088
WO WO-2022104412 A1 * 5/2022 ........... A61B 5/7264

OTHER PUBLICATIONS

Atasoy, et al., "Harmonic Brain Modes: A Unifying Framework for Linking Space and Time in Brain Dynamics", In Journal of the Neuroscientist, vol. 24, Issue 3, Jun. 1, 2018, pp. 277-293.

(Continued)

*Primary Examiner* — Eric F Winakur
*Assistant Examiner* — Sienna C Pyle
(74) *Attorney, Agent, or Firm* — Newport IP, LLC; Benjamin A. Keim

(57) ABSTRACT

This disclosure provides techniques for efficiently identifying epileptiform discharges in brain scan data. Brain scan data from an epileptic patient is segmented into multiple windows. Features of the data are identified for each window and provided to a machine learning (ML) model trained on labeled brain scan data. The ML model ranks the windows according to the likelihood each contains an epileptiform discharge. The highest-ranked window is shown to a technician trained in interpreting brain scans. The technician provides feedback regarding whether the window contains an epileptiform discharge or not. The ML model is updated by an online learning process based on feedback from the technician. The remaining windows are re-ranked, and the next highest-ranked window is shown to the technician. This process repeats and the ML model improves based on the technician feedback. This greatly reduces the amount of technician time spent reviewing brain scan data.

20 Claims, 4 Drawing Sheets

(51) Int. Cl.

| | |
|---|---|
| ***G06N 3/045*** | (2023.01) |
| ***G06N 3/09*** | (2023.01) |
| ***G16H 50/50*** | (2018.01) |

(56) References Cited

OTHER PUBLICATIONS

Buzsaki, Gyorgy, "Rhythms of the Brain", Published by Oxford University Press, Aug. 3, 2006, 465 Pages.
Li, et al., "Distinguishing Epileptiform Discharges From Normal Electroencephalograms Using Adaptive Fractal and Network Analysis: A Clinical Perspective", In Journal of Frontiers in Physiology, vol. 11, Article 828, Aug. 5, 2020, 15 Pages.
Roopun, et al., "Temporal Interactions between Cortical Rhythms", In Journal of Frontiers in Neuroscience, vol. 2, Issue 2, Dec. 15, 2008, pp. 145-154.
Seneviratne, et al., "Characteristics of Epileptiform Discharge Duration and Interdischarge Interval in Genetic Generalized Epilepsies", In Journal of Frontiers in Neurology, vol. 9, Article 36, Feb. 19, 2018, 10 Pages.
Smith, et al., "Human Interictal Epileptiform Discharges are Bidirectional Traveling Waves Echoing Ictal", In Journal of Elife, vol. 11, Jan. 20, 2022, 20 Pages.

* cited by examiner

EFFICIENT IDENTIFICATION OF EPILEPTIFORM DISCHARGES IN BRAIN SCAN DATA

BACKGROUND

Epilepsy is a serious neurological disorder characterized by abnormal brain activity causing seizures or periods of unusual behavior, sensations and sometimes loss of awareness. Seizures are caused by bursts of electrical activity in the brain. When medicines do not provide adequate control of seizures, surgery is an option. With epilepsy surgery, a surgeon removes the area of the brain where the seizures occur. Surgery is typically performed when analysis of brain scans indicate that the seizures originate in a small, well-defined area of the brain. Thus, detailed analysis of brains scans is necessary to identify precisely where seizures are occurring.

A trained technician may spend many hours reviewing brain scan data from a single session to identify the locations of epileptic seizures in the brain. The technician painstakingly goes through the brain scan data sequentially looking for ictal patterns, specifically epileptiform discharges of electrical activity for epileptic seizure onset zone localization. An ictal pattern refers to the changes in brainwave activity that can be detected by a brain scan during the ictal phase of a seizure. Epileptiform discharges are defined as generalized polyspikes, polyspike-wave, and spike-wave occurring in the form of a single discharge or a burst. These discharges are transients with a characteristic "spiky" morphology.

Manual review by a technician is inefficient. Currently, the availability of qualified technicians and the time required for a technician to review a brain scan are a bottleneck that can delay surgery. Delays while waiting for technicians also result in the underutilization of expensive machines such as magnetoencephalography (MEG) scanners. If technician time was not a bottleneck, the machines that generate brain scans could be used more fully resulting in a lower cost per scan. Improved techniques for the review of brain scans could increase technician efficiency and in turn, increase access to epilepsy surgery. This disclosure is made with respect to these and other considerations.

SUMMARY

This disclosure provides a statistics- and machine-learning-based approach to improving the efficiency of technicians by presenting multiple portions or "windows" of brain scan data in an order based on the likelihood that each window of data shows epileptiform discharges indicating epileptic spiking activity. The order in which the windows are presented is determined by a machine learning (ML) model trained on labeled examples of epileptiform discharges in brain scan data. The ML model is updated based on feedback received from the technician while he or she reviews the brain scan data. When presented with a window of the brain scan data, the technician can label the window as containing an epileptiform discharge, not containing an epileptiform discharge, or indicate that he or she is unsure if an epileptiform discharge is shown. The label provided by the technician is used to update the ML model while the technician is reviewing the brain scan data. Thus, the ML model becomes more accurate as the technician provides feedback.

The next most likely window to contain spike, as identified by the updated ML model, is then presented to the technician. This process repeats each time showing the technician another window of the brain scan data that he or she has not previously seen. The ML model creates a ranked list of the windows. The highest-ranked window is the one that is most likely to contain an epileptiform discharge. As feedback from the technician is incorporated, the ML model is updated, and the ranked order of the windows can dynamically change. The "top" window from the then current list is presented to the technician.

The technician continues reviewing the brain scan data until he or she has seen enough epileptiform discharges for the location in the brain of the epileptic seizure to be identified. Because the most relevant segments of the brain scan data are presented first, the technician can quickly find the windows that contain epileptiform discharges without reviewing the entire set of data. In some cases, the technician may be able to review the relevant portions of the brain scan data in a few minutes rather than the several hours it typically takes to review all the brain scan data from a single session. This provides significant time savings and greatly increases the efficiency of the technician.

Features and technical benefits other than those explicitly described above will be apparent from a reading of the following Detailed Description and a review of the associated drawings. This Summary is provided to introduce a selection of concepts in a simplified form that are further described below in the Detailed Description. This Summary is not intended to identify key or essential features of the claimed subject matter, nor is it intended to be used as an aid in determining the scope of the claimed subject matter. The term "techniques," for instance, may refer to system(s), method(s), computer-readable instructions, module(s), algorithms, hardware logic, and/or operation(s) as permitted by the context described above and throughout the document.

BRIEF DESCRIPTION OF THE DRAWINGS

The Detailed Description is described with reference to the accompanying figures. In the figures, the left-most digit(s) of a reference number identifies the figure in which the reference number first appears. The same reference numbers in different figures indicate similar or identical items. References made to individual items of a plurality of items can use a reference number with a letter of a sequence of letters to refer to each individual item. Generic references to the items may use the specific reference number without the sequence of letters.

DETAILED DESCRIPTION

Figure 1:
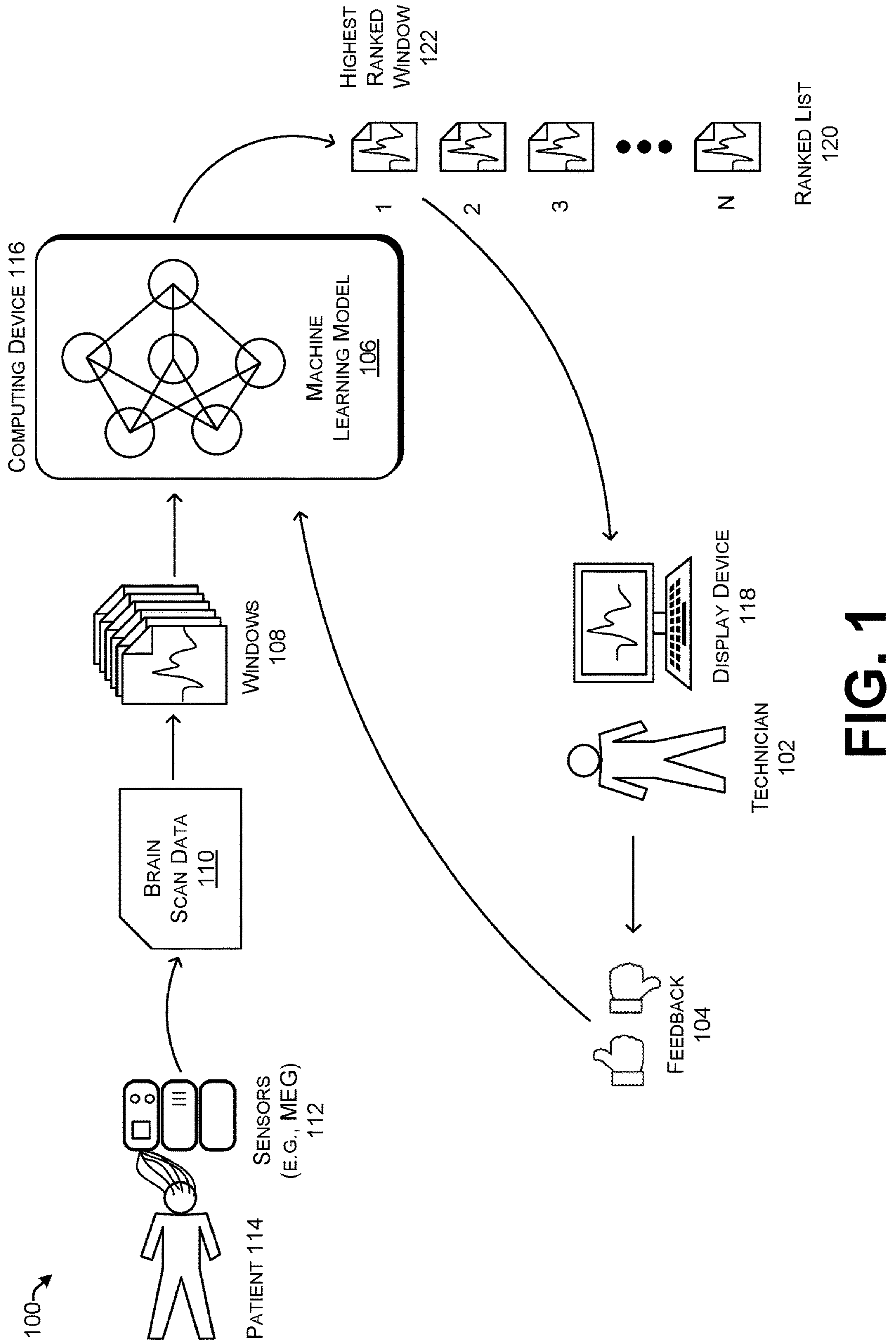
FIG. 1 is a diagram showing a technique for identifying epileptiform discharges in brain scan data with a human-in-the-loop ranking technique.

Brain imaging techniques such as, but not limited to, functional magnetic resonance imaging (fMRI), electroencephalography (EEG), magnetoencephalography (MEG), and intracranial electroencephalography (iEEG) can be used to diagnose and treat epilepsy. Neuroscientists use these brain imaging techniques to detect abnormal biosignals in the brain, which are often referred to as "spikes." These spikes are brief, high-frequency bursts of electrical activity that occur in specific regions of the brain. They are indicative of the underlying epileptic activity that is causing seizures.

EEG is the most common method used to identify spiking activity in the brain. EEG electrodes are placed on the scalp, and the electrical activity of the brain is recorded as a series of waveforms. In an epileptic brain, these waveforms may contain sharp spikes or brief bursts of high-frequency activity that are indicative of seizure activity. MEG is a technique that measures small fluctuations in the magnetic fields produced by the electrical activity of the brain. Like EEG, MEG can detect spikes and other abnormal electrical activity associated with epilepsy. fMRI is a non-invasive imaging technique that measures changes in blood flow in the brain, which is an indirect measure of neural activity. While fMRI is not as sensitive to spikes as EEG and MEG, it can still provide valuable information about the location and timing of epileptic activity in the brain. iEEG measures electrical activity in the brain by placing electrodes directly on the surface of the brain or inserting them into the brain tissue. iEEG provides a higher level of detail than scalp EEG and can help pinpoint the exact location of epileptic activity in the brain.

By analyzing the location, timing, and characteristics of these spikes, neuroscientists can identify the regions of the brain that are most affected by epilepsy and develop targeted treatment strategies. For example, surgical interventions can be used to reduce abnormal activity in these regions and prevent seizures from occurring. Therefore, the detection of spikes in brain imaging data plays an important role in the diagnosis and treatment of epilepsy.

During brain imaging, an epileptic patient may be connected to sensors for about 2 to 5 hours with the hopes that an observable epileptic seizure will occur. Currently, a technician reviews the brain scan data manually looking for spikes that indicate epileptic activity. The technician may scroll through several hours of data looking for spiking activity. Depending on the type of sensors used, the recordings may include as many as 1,200 data points per second. Reviewing this volume of data may require about 10 hours of technician time for each brain scan session. This is inefficient because the technician spends a large amount of time reviewing brain activity that is not associated with epileptic events.

Once the brain scan data that indicate epileptic seizures are identified, that data can be used to determine where in the brain abnormal electrical activity is occurring. This is done through a technique known as source localization. Source localization uses established techniques to determine where the electrical activity occurred within a 3D map of the brain based on the specific electrodes or other sensors that detected a spike. Dipole source localization using EEGs, or other sensing devices, recorded from the scalp is one technique used to make estimates of the locations of sources of electrical activity in the brain. This and other existing model-based imaging techniques can be used to perform source localization once the spikes in the brain scan data are identified. Currently, source localization is performed after the technician has reviewed the entire brain scan data from a particular patient session and identified the epileptiform discharge. The result of source localization which is the determination of the specific region within the 3D map of the brain is used to guide epileptic surgery.

The contents of this disclosure improve upon current techniques by using ML to assist the technician in rapidly identifying those portions of brain scan data that show a spike. By presenting these portions of the brain scan data to the technician first, rather than reviewing the entire brain scan sequentially, he or she can quickly identify the spiking activity without reviewing hours of data. The technician may be able to find the portions of the brain scan data that show the epileptiform discharge after reviewing only a small percentage (e.g., 1%, 5%, 10%) of the total data. This makes it possible for the technician to complete work in five or 10 minutes which used to require 10 hours. With this increase in efficiency, a technician can review brain scan data from multiple sessions in a single day. Eliminating this bottleneck can decrease wait times for epilepsy surgery.

FIG. 1 is a diagram 100 showing a human-in-the-loop technique for a technician 102 to provide feedback 104 that improves a ML model 106 for identifying epileptiform discharges in brain scan data 110. Brain scan data 110 is generated from sensors 112 connected to a patient 114. The patient 114 is connected to the sensors 112 with the hope of detecting an epileptic seizure event. The sensors 112 may be any type of sensor used for detecting brain activity and/or epileptic seizures. For example, the sensors 112 may be electrodes that are part of a fMRI, EEG, MEG, or iEEG system. The brain scan data 110 represents the data collected from the sensors 112 during a single session of monitoring brain activity of the patient 114. In a given session, and thus a given set of brain scan data 110, there may be no epileptic events, a single epileptic event, or more than one epileptic event. Because the sensors 112 monitor the brain activity of the patient 114 throughout the session, the brain scan data 110 is timeseries data. Typically, there are multiple sensors 112 collecting data for the patient 114, thus the brain scan data 110 may be multivariate data. However, it is also possible for the brain scan data 110 to be univariate data generated by a single sensor 112. Thus, the brain scan data 110 may be multivariate timeseries data or univariate timeseries data.

A single session of monitoring may collect brain scan data 110 for multiple hours (e.g., 1 or 2). This brain scan data 110 is divided into multiple shorter segments referred to as "windows" 108. The windows 108 may overlap with each other or they may be non-overlapping. An individual window contains a short segment of the brain scan data 110. The length of each window 108 may be set arbitrarily. For example, a single window 108 could contain about one second of the brain scan data 110. In some implementations, the lengths of the windows 108 may be set by the technician 102. Thus, the brain scan data 110 for a single session may be divided into many hundreds or thousands of windows 108.

The timeseries data contained in each of the windows 108 is converted into one or more numerical vectors that can be provided to the ML model 106 through a process known as featurization. Featurization refers to the process of extracting and transforming raw data into features that can be effectively utilized by ML models. This transformation is used for tailoring the data into a format that improves the models' performance and accuracy. As part of this process, pre-processing steps such as de-noising, normalization, size adjustment, and projection methods may be employed to refine the raw data. Featurization can be integrated as a part of the ML models themselves or, alternatively, separate ML models may be employed to learn a set of features from the data. The brain scan data 110 is then represented using some or all of these features in a format suitable for ML algorithms. The goal of feature extraction is to capture the most informative and discriminative aspects of the data that are relevant to identifying epileptiform discharges. There are many suitable techniques known to those of skill in the art for performing feature extraction from timeseries data.

For example, statistical measures of the brain scan data 110 may be used as features. These types of statistics-based methods may be purely unsupervised. The statistical measures may include one or more of average band power, mean, variance, skewness, kurtosis, absolute magnitude of deviations from average values, and other measures that describe the distribution of timeseries data. The bands are the delta (1-4 Hz), theta (4-8 Hz), alpha (8-13 Hz), beta (13-30 Hz), and gamma (30-80 Hz) bands used to measure neural activity with EEG and MEG systems. See Atasoy, S., Deco, G., Kringelbach, M. L., & Pearson, J. (2018). Harmonic brain modes: A unifying framework for linking space and time in brain dynamics. The Neuroscientist, 24(3), 277-293; Buzsáki, G. (2006). Rhythms of the brain. Oxford: Oxford University Press; and Roopun, A. K., Kramer, M. A., Carracedo, L. M., Kaiser, M., Davies, C. H., Traub, R. D., . . . . A., W. M. (2008). Temporal interactions between cortical rhythms. Frontiers in Neuroscience, 2(2), 145-154. The features may also be transform-based features. Transform-based features involve applying mathematical transforms to the raw data, such as Fourier transforms, wavelet transforms, or frequency-domain analysis. These transforms can reveal patterns in the data that are not readily apparent in the raw form.

Another technique for extraction features from brain scan data 110 involves capturing statistical dependencies from the data in a connected graph. This technique is described in US Patent Application titled "A Statistical Dependence-Aware Biological Predictive System" having docket number 410746-US-NP. With this technique, multivariate timeseries brain scan data is divided into windows, statistical dependencies are calculated between the windows of the timeseries data collected by separate sensors, a relationship matrix is generated as a function of the statistical dependencies, and the relationship matrix is transformed to generate a feature vector that captures statistical dependencies amongst the sensors for each of the windows.

Once features are extracted from the windows 108 by any of the above techniques or by different techniques, any combination of these features can be provided to the ML model 106. In an implementation, all available features are provided to the ML model 106 and those features that have little or no relevance to identifying epileptiform discharges are given a low or zero weight. In another implementation, featurization is used to select just the most relevant features and by doing so it reduces the dimensionality of the brain scan data 110.

The ML model 106 may be any type of ML model capable of generating a ranked list. In one implementation, ML model 106 contains one or more neural networks such as a recurrent neural network (RNN), Long Short-Term Memory (LSTM) neural network, a gated recurrent unit (GRU), a transformer, or a temporal fusion transformer. The ML model 106 may be initially trained using an offline training process on a labeled data set that has epileptiform discharges representing epileptic activity manually labeled as such. This training data set may include "stereotypical" representations of epileptiform discharges that are used to train the ML model 106 with a supervised pattern recognition technique. In an implementation, the ML model 106 is trained on previously labeled windows 108 from brain scans of other patients. Thus, the ML model 106 learns the features found in a standard epileptiform discharge. The ML model 106 may be implemented using a standard machine learning workflow such as (1) data cleaning and preprocessing, (2) data exploration and understanding, (3) feature engineering and selection, (4) model selection and training, (5) model evaluation, and (6) model optimization.

A computing device 116 maintains the ML model 106. The computing device 116 may be any type of conventional computing device including a plurality of physically separate computing devices such as a network-accessible or cloud-based computing device. In some implementations, the computing device 116 may be directly connected to a display device 118 used by the technician 102. However, in other implementations, the computing device 116 may be located elsewhere such as a server or cloud-based implementation.

The ML model 106 generates a ranked list 120 of the windows 108. The ranked list 120 may be generated by any conventional learning to rank technique. Examples of learning to rank techniques or machine-learned ranking algorithms known to those of ordinary skill in the art include, but are not limited to, RankNet, LambdaRank, LambdaMART, RankSVM, RankBoost, GBRank, and FRank. The windows 108 can also be ranked by the posterior probabilities returned by the ML model 106. The posterior probability represents the probability that an item belongs to a particular class or category, given the observed data. At this stage, the ranked list 120 is generated solely based on the prior training of the ML model 106. The windows 108 are ranked from most likely to contain a spike to least likely to contain a spike. In the ranked list 120, there is one highest-ranked window 122. The highest-ranked window 122 represents that segment of the brain scan data 110 assessed by the ML model 106 as having the highest likelihood of containing an epileptiform discharge.

The highest-ranked window 122 is shown to the technician 102 on the display device 118. The technician 102 reviews the portion of the brain scan data 110 contained in the highest-ranked window 122 and determines if shows a spike caused an epileptic seizure. With this technique, technician 102 is not reviewing the brain scan data 110 sequentially in order that it was collected but is looking first at a segment identified by the ML model 106 as likely showing an epileptiform discharge.

It will be relatively easy for the ML model 106, once initially trained, to distinguish between windows 108 that include some type of spike and those that contain data which is relatively flat. The greater challenge is to differentiate between polyspikes, polyspike-waves, and spike-waves caused by epileptiform discharges and spikes caused by "noise" such as the patient 114 blinking his or her eyes or moving his or her head. The spikes caused by "noise" can also appear as spikes in the timeseries data and thus may have similar features to epileptiform discharges. Without refinement and further training, the ML model 106 may have difficulty distinguishing between "noise" spikes and epileptiform discharges caused by epileptic seizures.

The technician 102 reviews the portion of the brain scan data 110 contained in the highest-ranked window 122. He or she determines if it shows an epileptiform discharge or not. The training of the technician 102 enables him or her to distinguish between true epileptiform discharges and false positives. The technician 102 provides feedback 104 indicating whether or not the highest-ranked window 122 contains an epileptiform discharge. The feedback 104 is provided to the ML model 106.

The ML model 106 is updated using a process known as online learning to incorporate the feedback 104. Thus, ML model 106 is updated based on the additional label provided by the technician 102 for the data in the highest-ranked window 122. If the highest-ranked window 122 shows an epileptiform discharge, the feedback 104 from the technician 102 will be used by the ML model 106 as positive feedback. If, however, the ML model 106 identifies data that does not include an epileptiform discharge as the highest-ranked window 122, the feedback 104 from the technician 102 will be negative feedback. There are many known techniques for implementing online learning to update a ML model based on feedback. Persons of ordinary skill in the art in the art will be able to readily adapt existing online learning techniques to incorporate in the feedback 104 and modify the ML model 106.

The windows 108 may be re-ranked by the ML model 106 as updated following the feedback 104 from the technician 102. The re-ranking may or may not result in a different ordering of the windows 108 in the ranked list 120. The window 108 that was previously the highest-ranked window 122 has already been considered by the technician 102 and will not be presented again. The highest-ranked window 122 from the ranked list 120 as it currently exists is then presented on the display device 118 to the technician 102. This window may be thought of as the second-highest-ranked window (because the first highest-ranked window was previously shown to the technician 102 and then removed from further consideration). The technician 102 again provides feedback 104 on this window and the ML model 106 is again updated. This process continues as the technician 102 reviews the windows 108. In some implementations, the technician 102 may review a batch of windows before the ML model 106 is updated. The technician 102 is not reviewing the windows 108 in the order in which they exist in the timeseries but is reviewing them in the order they are ranked by the ML model 106. As the review of the windows 108 by the technician 102 proceeds, false positives will place lower in the ranked list 120 and windows 108 showing actual epileptiform discharges will move toward the top of the ranked list 120. Ideally, the windows 108 at the top of the ranked list 120 will all include epileptiform discharges. Thus, by reviewing only a small percentage of the total number windows 108, the technician 102 will be able to identify all the portions of the brain scan data 110 that show epileptiform discharges.

Figure 2:
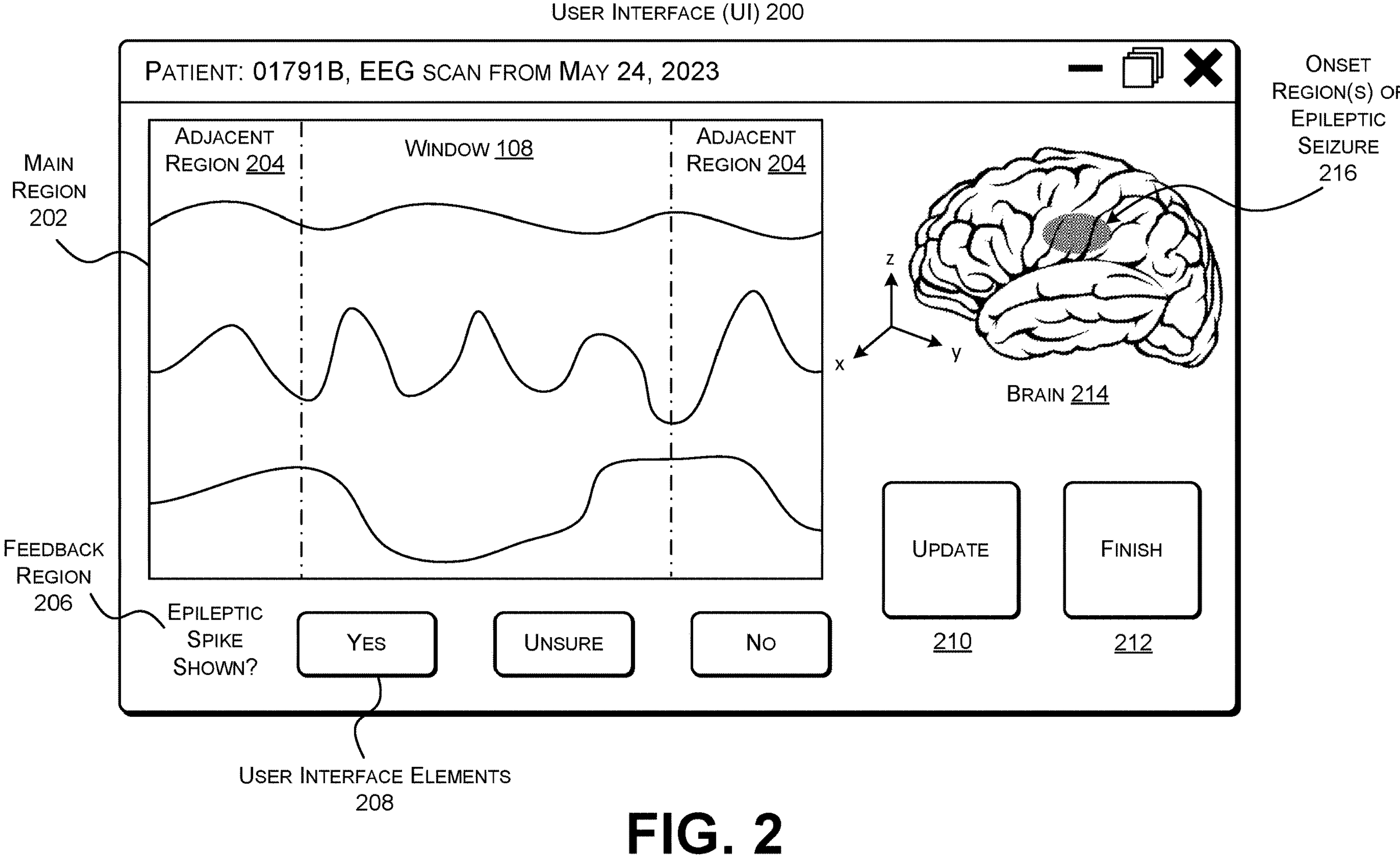
FIG. 2 is a diagram of an illustrative user interface for a technician to review brain scan data.

FIG. 2 shows an illustrative user interface (UI) 200 for a technician to view and provide feedback on brain scan data. The UI 200 may be presented, for example, on the display device 118 shown in FIG. 1. The UI 200 includes a main region 202 that shows one of the windows 108 of the brain scan data. In an implementation, only a single window 108 may be displayed in the main region 202. Thus, depending on the length of a window 108, the main region 202 may show only one or a few seconds of the brain scan data. In an implementation, the main region 202 may also include an adjacent region 204 on one or both sides of the window 108. The adjacent region(s) 204 include additional brain scan data temporally contiguous with that of the window 108. This provides the technician with greater context to interpret the data shown in the window 108. The portion of the brain scan data that corresponds to the window 108 may be emphasized or otherwise distinguished from the brain scan data that appears in the adjacent region(s) 204. For example, the window 108 may be emphasized through highlighting or delineated by dashed lines.

The UI 200 also includes a feedback region 206. The feedback region 206 includes one or more user interface elements 208 that are actuable by the technician to provide feedback. For example, the user interface elements 208 may include a series of buttons with which the technician can indicate "yes," "no," or "unsure" based on his or her assessment of whether or not an epileptiform discharge is shown in the window 108. Alternate types of user interface elements 208 may also be used. For example, the feedback region 206 could include a slider or a dial with which the technician is able to indicate a value along a spectrum such as 0-100% representing confidence that an epileptiform discharge is shown. In an implementation, the feedback provided by the technician is binary feedback (e.g., yes or no). In another implementation, the feedback is scaled feedback such as a number from 1 to 5 or 1 to 100.

In one implementation, the next window from the ranked list is automatically displayed in the main region 202 after the user interacts with the user interface elements 208 in the feedback region 206. That is, the window 108 of brain scan data in the main region 202 is replaced with a different window 108 of brain scan data that is not temporally contiguous. Thus, the technician does not need to provide any additional commands or interact with any other portion of the UI 200 in order to advance through to the next window. This increases the speed with which the technician can review and label the windows.

The system may update the ML model after each instance in which the technician provides feedback. However, there may be a delay while the ML model is updated. Thus, in some implementations, the ML model may not be updated after each window is reviewed. The technician may review a batch of windows before the feedback is used to update the ML model. For example, the system may only update the ML model after the technician has reviewed, for example, 3-10 windows. The UI 200 may include a user interface element such as an "update" button 210 with which the technician can manually instruct the ML model to update based on the feedback received since the last update. Thus, the technician may be able to control when the feedback is used to update the ML model.

The UI 200 may also include a "finish button" 212 or other type of user interface element with which the technician can indicate that he or she has reviewed enough brain scan data to identify the windows that contain epileptiform discharges. This allows the technician to stop reviewing the brain scan data from a given patient session. The technician saves time by not reviewing portions of the brain scan data that do not contain epileptiform discharges. However, the technician is also able to review every window—the full set of brain scan data—if desired. If the technician 212 activates the "finish button" 212, or similar user interface element, the system may then automatically replace the brain scan data that is currently displayed with brain scan data from another patient session.

The UI 200 can also include a 3D rendering of a brain 214 that is used to visualize the location of an onset region(s) of an epileptic seizure 216 as determined from the epileptiform discharges in the brain scan data. There may be one or more discrete regions of the brain 214 indicated as a possible onset region of an epileptic seizure 216. The rendering of the brain 214 and the location of the onset region of the epileptic seizure 216 may be generated using techniques for source localization known in the art. Each window identified as containing an epileptiform discharge provides additional data that can be used for source localization. The process of source localization may be repeated each time an additional window is identified by the technician as containing an epileptiform discharge. Thus, instead of waiting until the technician has reviewed all the brain scan data from a given session to calculate the site of the epileptic seizure in the patient's brain, source localization can be performed as the technician reviews the brain scan data.

The location of the onset region(s) of an epileptic seizure 216 in the patient's brain 214 may be visualized in many different ways. In one implementation, a region (e.g., sphere) may represent the suspected location and become smaller or move as more epileptiform discharges are identified and the results of source localization become more precise. In one implementation, the location of the onset region of the epileptic seizure 216 is shaded and an intensity of the shading (e.g., becoming darker) or a color of the shading changes as the system gains greater confidence and certainty about the results of the source localization. The level of certainty or confidence level may be presented as a probability measurement. Thus, in some implementations, a visual appearance of the indication of the location in the brain of the onset region of the epileptic seizure 216 changes based on a confidence level determined from feedback provided by the technician in the feedback region 206. The confidence level in the accuracy of the location of the epileptic seizure 216 may be indicated by the visual appearance of the rendering of the brain 214. If there are multiple onset regions of an epileptic seizure 216 shown, each may be labeled with a respective level of certainty that it represents a location of onset of an epileptic seizure. Windows 108 that are used to identify a given onset region of an epileptic seizure 216 may also be associated with that region to provide support and evidence for the source localization. In an implementation, interaction (e.g., clicking on) with an onset region of an epileptic seizure 216 shown in the brain 214 may cause the UI 200 to display the windows 108 that were used to identify the onset region.

As mentioned above, the windows that contain epileptiform discharges are used to determine a location of the epileptic seizure 216 in the patient's brain 214. Performing source localization and including a rendering of the brain 214 on the UI 200 enables the technician to see when he or she has extracted enough information from the brain scan data for a surgeon to operate. At this point the technician can then stop reviewing the brain scan data.

Figure 3:
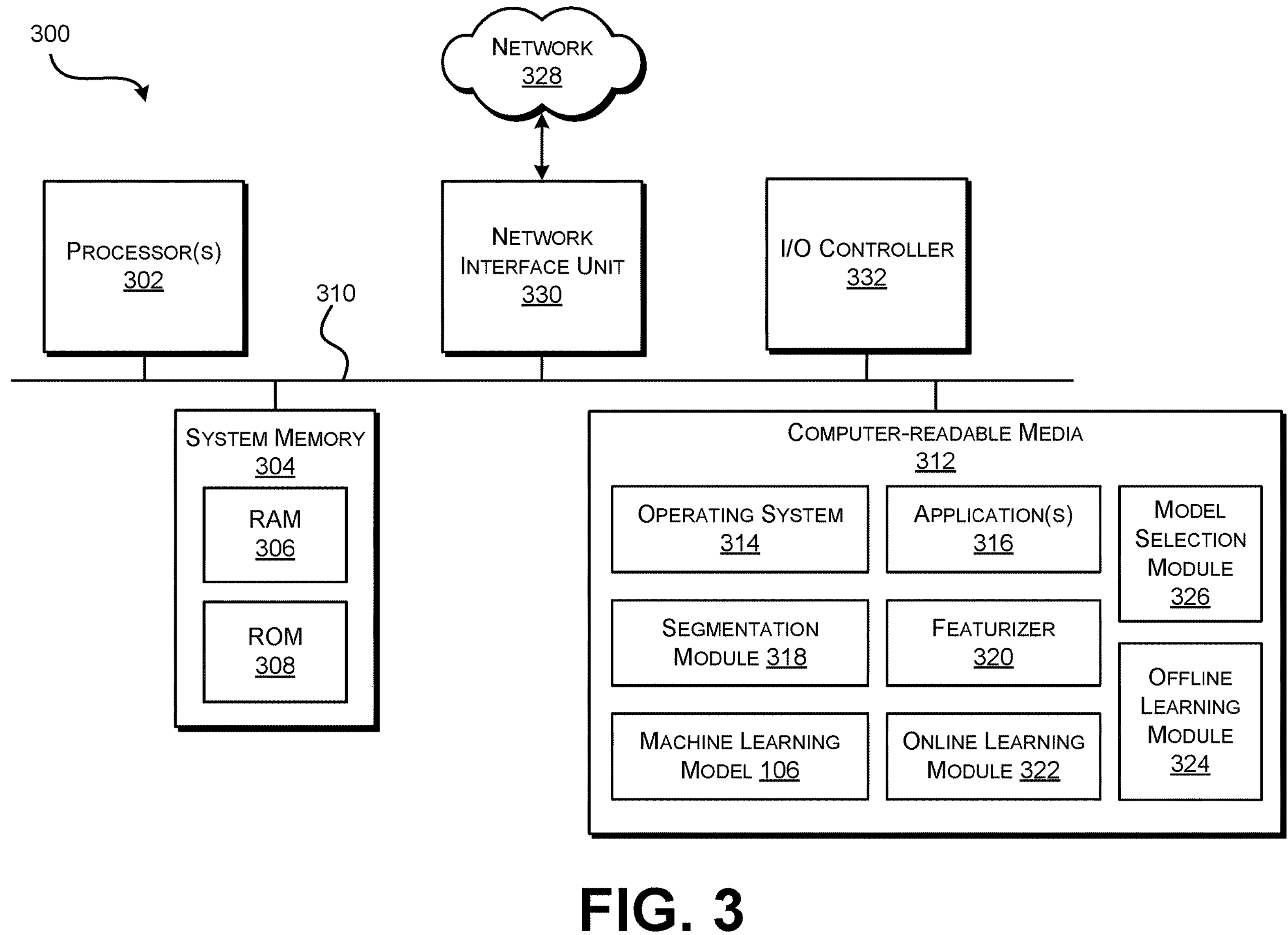
FIG. 3 is a computer architecture diagram illustrating an illustrative computer hardware and software architecture for a computing device capable of implementing aspects of the techniques and technologies presented herein.

FIG. 3 shows details of an example computer architecture 300 for a device, such as a computer or a server configured as part of a cloud-based platform, capable of executing computer instructions (e.g., a module or a component described herein). For example, the device may be the computing device 116 shown in FIG. 1. The computer architecture 300 illustrated in FIG. 3 includes one or more processor(s) 302, a system memory 304, including a random-access memory 306 ("RAM") and a read-only memory ("ROM") 308, and a system bus 310 that couples the memory 304 to the processors(s) 302. The processor(s) 302 may also comprise or be part of a processing system. In various examples, the processor(s) 302 of the processing system are distributed. Stated another way, one processor(s) 302 of the processing system may be located in a first location (e.g., a rack within a datacenter) while another processor(s) 302 of the processing system is located in a second location separate from the first location.

Processing unit(s), such as processor(s) 302, can represent, for example, a CPU-type processing unit, a GPU-type processing unit, a field-programmable gate array (FPGA), another class of digital signal processor (DSP), or other hardware logic components that may, in some instances, be driven by a CPU. For example, illustrative types of hardware logic components that can be used include Application-Specific Integrated Circuits (ASICs), Application-Specific Standard Products (ASSPs), System-on-a-Chip Systems (SOCs), Complex Programmable Logic Devices (CPLDs), and the like.

A basic input/output system containing the basic routines that help to transfer information between elements within the computer architecture 300, such as during startup, is stored in the ROM 308. The computer architecture 300 further includes a computer-readable media 312 for storing an operating system 314, application(s) 316, modules/components, and other data described herein. Examples of modules/components that may be stored in the computer-readable media 312 and comprise computer-executable instructions implemented by the processor(s) 302 are a segmentation module 318, a featurizer 320, the ML model 106 introduced in FIG. 1, an online learning module 322, and offline learning module 324, and a model selection module 326.

The segmentation module 318 is configured to segment brain imaging data into a plurality of windows. The segmentation module 318 may use any suitable process to divide a longer segment of timeseries data into shorter segments. The windows may all be the same length or there may be variations in the length of the windows. The windows may be non-overlapping or they may be overlapping. The length of a window created by the segmentation module 318 may be, for example, 1 to 30 seconds. The length of a window may be predetermined such as by coding of the segmentation module 318. Alternatively, the length of a window may be set for each segmentation task by input from a user.

The featurizer 320 is configured to extract one or more features from the plurality of windows. The featurizer 320 can perform feature extraction by extracting features from brain scan data that are relevant to spike in activity. In an implementation, the featurizer 320 may convert each window of brain scan data into a numerical vector. Thus, the featurizer 320 may take a complex signal and allow it to be analyzed in a lower dimensional space. The featurizer 320 may use any known technique for extracting features from timeseries data such as statistical-based features, transform-based features, graph-based features, or deep learning features. Deep learning techniques can be used to automatically extract features from raw data and recurrent neural networks (RNNs) are well-suited to learn features from sequential data.

The ML model 106 may be any type of ML model suitable for generating a ranked list of items. The ML model 106 will typically contain one or more neural networks. Multiple ML model architectures and designs are known to those of ordinary skill in the art for implementation learning to rank algorithms such as but are not limited to, RankNet, LambdaRank, LambdaMART, RankSVM, RankBoost, GBRank, and FRank. Persons of ordinary skill in the art will understand how to select and implement an appropriate ML model 106.

The online learning module 322 is configured to update the ML model based on feedback provided by the technician. The feedback from the technician may be provided through interaction with one or more user interface elements (e.g., buttons, slider bars, etc.) provided to the technician on a user interface. In general, the feedback from the technician indicates whether or not a window shows an epileptiform discharge. Assuming the technician is accurate, the feedback provides the "correct" answer with which the online learning module 322 can compare to the prediction made by the ML model 106 and measure the loss suffered by any difference.

With each piece of additional feedback received from the technician, the online learning module 322 attempts to improve the ability of the ML model 106 to correctly classify the contents of the window as showing a spike or not. The goal of online learning is to maximize the accuracy of the predictions made by the ML model 106 based on feedback from the technician. This contrasts with traditional batch or offline ML methods that are often designed to learn a model from the entire training data set at once. Once updated, the ML model 106 may be used to re-rank the remaining windows.

The offline learning module 324 is used to train the ML model 106 prior to use during a patient session. This can be the ML model 106 used initially before feedback is received from the technician. The offline learning module 324 creates a "global model" or a base model that can be used with any patient. In one implementation, the global model is a combination of trained models that includes the models generated from multiple patient sessions and multiple different patients. In one implementation, the global model is trained using labeled data from multiple patients, up to and including all available patient data, without creating any other models. Patient privacy is protected when creating the global model by training without using any personally identifiable features or information from specific individuals.

In some implementations, it may be built from all available ML models across all patients and all sessions available to the entity training the global model. The global model is trained on a large amount of training data but, it may be less accurate in some circumstances because it is not personalized to any individual patient. In one implementation, multiple patient-specific ML models from multiple different individuals are combined to make the global model. The global model can be updated based on the feedback from a technician. Thus, the work of multiple technicians at multiple locations across multiple different times may all be added to the body of training data used for the global model.

The model selection module 326 is configured to select the ML model 106 from multiple pre-existing ML models or to create an ensemble model from multiple pre-existing ML models. There may be multiple different pre-existing ML models capable of classifying segments of brain scan data as containing an epileptiform discharge or not. One or more of these models is selected as the starting point for classification that is further refined through technician feedback as described above.

If there are multiple pre-existing models, they may have different strengths and weaknesses. Some ML models may work better for EEG data while others work better for MEG data. Some may work better for children while others work better for adults. There may be ML models that are better able to identify noise caused by eye movement while other models are better at identifying noise caused by scalp muscle movement. The model selection module 326 functions to choose which of these is used as the ML model 106.

One type of pre-existing model can be a patient-specific ML model. An epileptic patient will likely have multiple brain scans during the course of treatment for the disease. If those brain scans are evaluated using the techniques of this disclosure, there will be a trained ML model generated for each brain scan. Each of these may be referred to as a per-session model. A patient-specific ML model represents a combination of multiple per-session models for the same patient.

A patient-specific model can be used for a patient who has had previous brain scans to provide a better starting model than the base model trained on data from multiple different patients. The patient-specific model will likely be more accurate than a single per-session model because it is trained on a larger set of data. The patient-specific model may also combine feedback and subjective opinions from different technicians. Thus, a patient-specific model can represent a baseline not only across different sessions but also across different technicians. This patient-specific model may exist in addition to one or more per-session models for the patient. Feedback from the technician may be used for updating the patient-specific ML model in parallel to updating a current per-session model. The patient-specific ML model can be used as the ML model 106 for initially identifying a window that is most likely to show an epileptiform discharge in a subsequent evaluation of different brain scan data from that patient.

The model selection module 326 can also be used to combine multiple models or create an ensemble model. There are many known techniques for combining multiple ML models. One way to combine models is through voting such as ensemble voting or ranked voting. Other ways to combine the predictions from multiple contributing models include bagging, random forest, and extra-trees ensemble. These techniques reduce model error while maintaining the model's generalization. Any of these or other techniques may be used by the model selection module 326.

The computer-readable media 312 is communicatively connected to processor(s) 302 through a mass storage controller connected to the bus 310. The computer-readable media 312 provides non-volatile storage for the computer architecture 300. Although the description of computer-readable media 312 contained may be implemented as a mass storage device, it should be appreciated by those skilled in the art that computer-readable media 312 can be any available computer-readable storage medium or communications medium that can be accessed by the computer architecture 300.

Computer-readable media can include computer-readable storage media and/or communication media. Computer-readable storage media can include one or more of volatile memory, nonvolatile memory, and/or other persistent and/or auxiliary computer storage media, removable and non-removable computer storage media implemented in any method or technology for storage of information such as computer-readable instructions, data structures, program modules, or other data. Thus, computer storage media includes tangible and/or physical forms of media included in a device and/or hardware component that is part of a device or external to a device, including RAM, static random-access memory (SRAM), dynamic random-access memory (DRAM), phase-change memory (PCM), ROM, erasable programmable read-only memory (EPROM), electrically erasable programmable read-only memory (EEPROM), flash memory, compact disc read-only memory (CD-ROM), digital versatile disks (DVDs), optical cards or other optical storage media, magnetic cassettes, magnetic tape, magnetic disk storage, magnetic cards or other magnetic storage devices or media, solid-state memory devices, storage arrays, network-attached storage, storage area networks, hosted computer storage or any other storage memory, storage device, and/or storage medium that can be used to store and maintain information for access by a computing device.

In contrast to computer-readable storage media, communication media embodies computer-readable instructions, data structures, program modules, or other data in a modulated data signal, such as a carrier wave, or other transmission mechanism. As defined herein, computer-readable storage medium does not include communication medium. That is, computer-readable storage media does not include communications media and thus excludes media consisting solely of a modulated data signal, a carrier wave, or a propagated signal, per se.

According to various configurations, the computer architecture 300 may operate in a networked environment using logical connections to remote computers through a network 328. The computer architecture 300 may connect to the network 328 through a network interface unit 330 connected to the bus 310. An I/O controller 332 may also be connected to the bus 310 to control communication in input and output devices.

It should be appreciated that the software components described herein may, when loaded into the processor(s) 302 and executed, transform the processor(s) 302 and the overall computer architecture 300 from a general-purpose computing system into a special-purpose computing system customized to facilitate the functionality presented herein. The processor(s) 302 may be constructed from any number of transistors or other discrete circuit elements, which may individually or collectively assume any number of states. More specifically, the processor(s) 302 may operate as a finite-state machine, in response to executable instructions contained within the software modules disclosed herein. These computer-executable instructions may transform the processor(s) 302 by specifying how the processor(s) 302 transitions between states, thereby transforming the transistors or other discrete hardware elements constituting the processor(s) 302.

Figure 4:
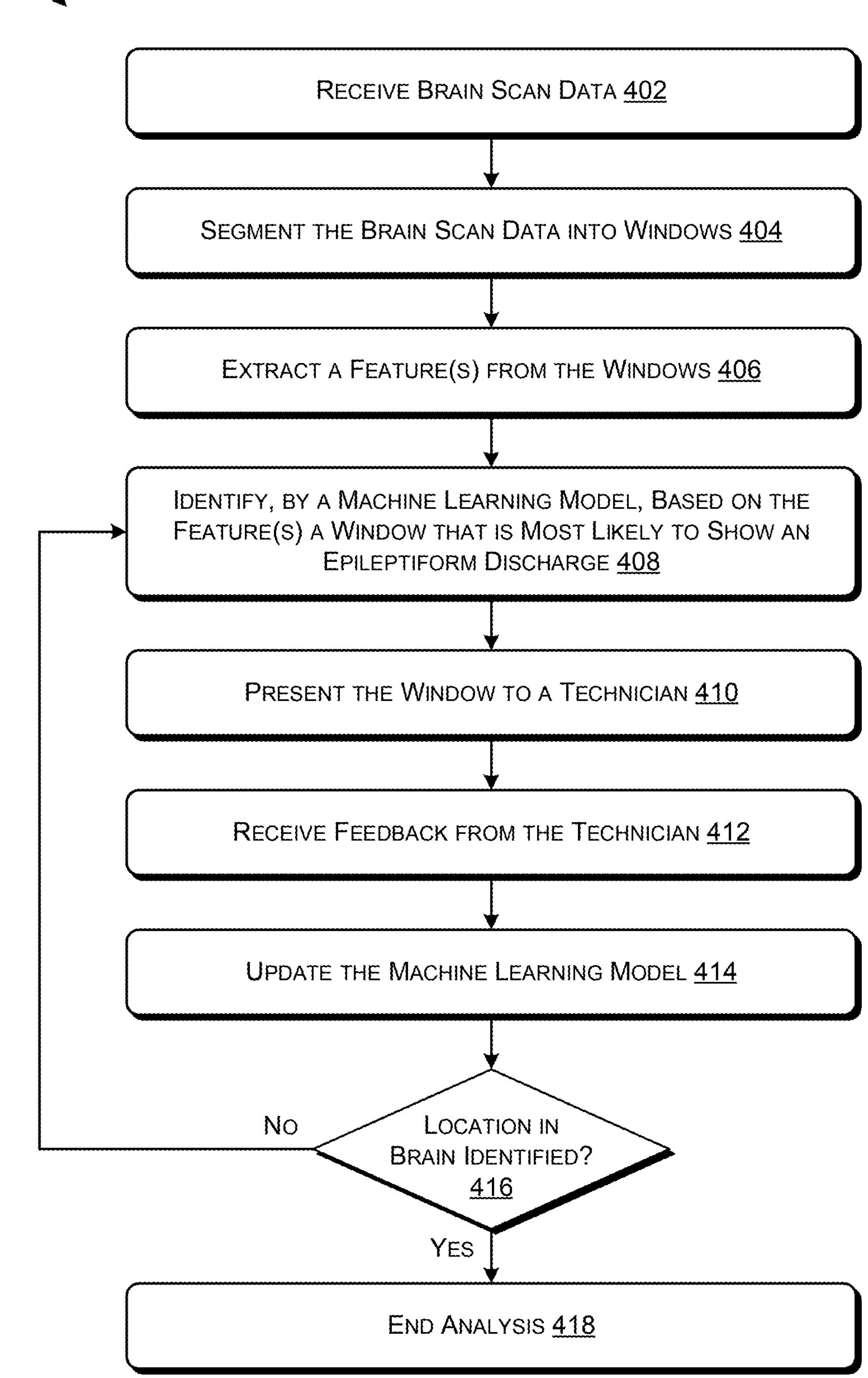
FIG. 4 is a flowchart of a method for identifying the location in the brain of epileptic seizures from brain scan data.

FIG. 4 is a flow diagram of an illustrative method 400 for identifying the location in the brain of epileptic seizures from brain scan data. Method 400 may be implemented using the techniques shown in FIG. 1 and may be implemented with the computer architecture shown in FIG. 3.

At operation 402, brain scan data is received. The brain scan data may be univariate or multivariate timeseries data. The brain scan data can be generated by any type of brain sensing technology including, but not limited to, functional magnetic resonance imaging (fMRI), electroencephalography (EEG), magnetoencephalography (MEG), and intracranial electroencephalography (iEEG).

At operation 404, the brain scan data is segmented into windows. The brain scan data is divided into multiple windows which may be of equal length or different lengths. The windows may be overlapping or non-overlapping. For example, the brain scan data may be divided into windows that are two seconds long and include a 0.5 second overlap with the proceeding and following window.

At operation 406, one or more features are extracted from the windows. The feature extraction may be performed by a featurizer. Extraction of the one or more features from the plurality of windows may be performed by a supervised or an unsupervised method based on one or more statistical features of the brain scan data. For example, the one or more statistical features can be any of average band power, mean, variance, skewness, or kurtosis. In an implementation, extracting one or more features from the plurality of windows is performed by generating a connected graph from the brain scan data and then generating a feature vector from the connected graph.

At operation 408, a window that is most likely to show epileptiform discharge is identified by ML model. The ML model identifies that window based on the features extracted at operation 406. The ML model may create a ranked list of the windows based on the likelihood that each window shows an epileptiform discharge through any one of multiple processes known as learning to rank. In this ranked list, the window on the "top" of the list is the window that is determined by the ML model to have the highest probability of showing an epileptiform discharge. Thus, the window is identified as the most likely to show an epileptiform discharge based on its position as the highest-ranked window in the list. This may be a primary ML model or an initial ML model that ranks the windows prior to receiving any technician feedback for this set of brain scan data.

At operation 410, the window is presented to a technician. The window may be presented to the technician in a user interface such as the user interface shown in FIG. 2. The technician can then review the brain scan data contained in the window to determine if it shows an epileptiform discharge or not.

At operation 412, feedback is received from the technician. The feedback from the technician indicates the likelihood that the window shows an epileptiform discharge. The technician may provide binary feedback i.e., spike yes or no. Alternatively, the technician may provide data indicating a level of confidence that the window shows an epileptiform discharge. The feedback from the technician may be provided in the same user interface that displays the window to the technician.

At operation 414, the ML model is updated based on the feedback received from the technician. Updating the ML model creates a modified ML model. Updating the ML model can be performed by any number of known techniques for implementing online learning or fine-tuning a ML model. For example, the ML model may be updated by modifying a learning to rank algorithm used to rank the plurality of windows with an online learning technique that uses the feedback from the technician as a label for supervised training. In one implementation, updating the ML model comprises updating feature weights applied to the one or more features from the plurality of windows. Updating the ML model may also be implemented by updating the weights of edges that connect nodes in a neural network or by forming or breaking connections between nodes in a neural network.

At operation 416, an indication may be received from the technician that the location of the onset region of epileptic seizure in the brain of the patient can be identified. If, based on the identified epileptiform discharges in the brain scan data, it is not yet possible to localize where the epileptic seizure originated, method 400 will proceed along the "no" path and return to operation 408. Operations 408-416 are repeated as the technician continues to review more windows and provide feedback. The technician will typically continue reviewing the brain scan data until the location in the patient's brain of the epileptiform discharges can be identified with at least a threshold level of certainty or confidence. A visualization of a brain showing a predicted location for the epileptiform discharges based on the feedback from the technician may be generated as shown in FIG. 2 to assist the technician in making this determination. At this point, the technician may indicate that he or she no longer needs to review additional windows, and method 400 proceeds along the "no" path to operation 418.

During each iteration as the technician reviews windows, the ML model is updated based on the feedback. Windows that have already been reviewed by the technician are removed from the list and the remaining windows are re-ranked by the modified ML model. An existing ranked list of the windows may be re-ordered. Alternatively, the windows may be ranked anew creating a new ranked list with a different order. Thus, after a first window has been evaluated by the technician, the modified ML model identifies a second window from the plurality of windows that is most likely to show an epileptiform discharge. The second window is the window on the top of the ranked list generated by the modified ML model. This process retrains a classifier, the ML model, based on sparse rankings provided by the technician.

In some implementations, only a subset of the windows are re-sorted. For example, if the brain scan data is divided into many thousands of windows, the modified ML algorithm may be used to re-sort only the highest-ranked windows 122. This can be referred to as a "consideration set." Applying the modified ML model to re-sort only a subset of the windows can reduce latency and processor cycles. Many of the windows that are ranked lower in the ranked list by the initial sorting are unlikely to contain spikes. Thus, these windows will likely never be reviewed by a technician and updating the ranking of these windows may be of little consequence. Refinements to the ML model are most useful for improving the ability to discriminate between windows that show actual epileptiform discharges and windows that show spikes caused by other activity-false positives. These will likely be found in the windows towards the top of the ranked list.

At operation 418, analysis of the brain scan data ends. In many instances, the technician may be able to identify enough spikes to calculate the location of the epileptic seizure after reviewing only 100 or 200 windows. This can represent a significant decrease in the amount of technician time required to review the brain scan data from a single session. The time savings may be as much as 90%, 95%, 98%, 99%, or more.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A method of identifying epileptiform discharges in brain scan data comprising:

a) receiving the brain scan data;
b) segmenting the brain scan data into a plurality of windows;
c) extracting one or more features from the plurality of windows;
d) identifying, by a machine learning model, based on the one or more features a first window from the plurality of windows that is most likely to show an epileptiform discharge;
e) presenting the first window to a technician;
f) receiving feedback from the technician on a likelihood that the first window shows an epileptiform discharge;
g) updating the machine learning model based on the feedback from the technician to create a modified machine learning model; and
h) identifying, by the modified machine learning model, a second window from the plurality of windows that is most likely to show an epileptiform discharge.

Clause 2. The method of clause 1, wherein the brain scan data is generated by one of functional magnetic resonance imaging (fMRI), electroencephalography (EEG), magnetoencephalography (MEG), or intracranial electroencephalography (iEEG).

Clause 3. The method of any of clauses 1 to 2, wherein extracting one or more features from the plurality of windows is based on one or more statistical features of the brain scan data.

Clause 4. The method of clause 3, wherein the one or more statistical features are average band power, mean, variance, skewness, or kurtosis.

Clause 5. The method of any of clauses 1 to 2, wherein extracting one or more features from the plurality of windows is performed by generating a connected graph from the brain scan data and then generating a feature vector from the connected graph.

Clause 6. The method of clauses 1 to 5, wherein identifying the first window from the plurality of windows that is most likely to show an epileptiform discharge comprises creating a ranked list of the windows based on the one or more features and identifying a highest-ranked window.

Clause 7. The method of any of clauses 1 to 6, wherein updating the machine learning model comprises updating feature weights applied to the one or more features from the plurality of windows.

Clause 8. The method of any of clauses 1 to 7, wherein updating the machine learning model comprises modifying a learning to rank algorithm used to rank the plurality of windows with an online learning technique that uses the feedback from the technician as a label for supervised training.

Clause 9. The method of any of clauses 1 to 8, further comprising repeating steps e)-h) until an indication is received from the technician that a location of an onset region of epileptic seizure in a brain can be identified.

Clause 10. The method of clause 9, further comprising updating at least one of a patient-specific machine learning model or a global model based on the feedback from the technician, wherein the patient-specific machine learning model or the global model is used as the machine learning model for initially identifying a window that is most likely to show an epileptiform discharge in a subsequent evaluation of different brain scan data.

Clause 11. The method of any of clauses 1 to 10, further comprising generating a visualization of a brain showing a predicted location for an onset region of epileptic seizure based on epileptiform discharges identified by the technician.

Clause 12. A computer-readable storage medium having computer-executable instructions encoded thereon to cause a computing device to perform the method of any of clauses 1 to 11.

Clause 13. A system for identifying epileptiform discharges in brain scan data comprising:

a processor; and
computer-readable media communicatively connected to the processor;

a segmentation module, stored in the computer-readable media and comprising computer-executable instructions implemented by the processor, configured to segment brain scan data into a plurality of windows;

a featurizer, stored in the computer-readable media and comprising computer-executable instructions implemented by the processor, configured to extract one or more features from the plurality of windows;

a machine learning model, stored in the computer-readable media and comprising computer-executable instructions implemented by the processor, configured to identify a first window from the plurality of windows that is most likely to show an epileptiform discharge based on the one or more features; and a display device, connected to the processor, configured to present the first window to a technician together with one or more user interface elements actuable by the technician to indicate a likelihood that the first window shows an epileptiform discharge.

Clause 14. The system of clause 13, further comprising an online learning module, stored in the computer-readable media and comprising computer-executable instructions implemented by the processor, configured to update the machine learning model based on feedback provided by the technician interacting with the one or more user interface elements.

Clause 15. The system of any of clauses 13 to 14, further comprising one or more sensors configured to detect brain activity and generate the brain scan data.

Clause 16. The system of any of clauses 13 to 15, further comprising a model selection module, stored in the computer-readable media and comprising computer-executable instructions implemented by the processor, configured to select the machine learning model from multiple pre-existing machine learning models or to create an ensemble model from the multiple pre-existing machine learning models.

Clause 17. A system for identifying epileptiform discharges in brain scan data comprising:

a means for processing (e.g., a processor); and a means for storing computer-executable instructions (e.g., computer-readable media) communicatively connected to the means for processing;

a means for segmenting, stored in the means for storing and comprising computer-executable instructions implemented by the means for processing, configured to segment brain scan data into a plurality of windows;

a means for featurizing, stored in the means for storing and comprising computer-executable instructions implemented by the means for processing, configured to extract one or more features from the plurality of windows;

a machine learning model, stored in the means for storing and comprising computer-executable instructions implemented by the means for processing, configured to identify a first window from the plurality of windows that is most likely to show an epileptiform discharge based on the one or more features; and a means for displaying (e.g., display device), connected to the means for processing, configured to present the first window to a technician together with one or more user interface elements actuable by the technician to indicate a likelihood that the first window shows an epileptiform discharge.

Clause 18. A user interface for identifying epileptiform discharges in brain scan data comprising:

a main region that displays a window of brain scan data; and a feedback region that displays one or more user interface elements actuable by a technician to indicate a likelihood that the window in the main region shows an epileptiform discharge.

Clause 19. The user interface of clause 18, wherein the one or more user interface elements of the feedback region are further configured to, upon actuation, replace the window of brain scan data in the main region with a different window of brain scan data that is not temporally contiguous.

Clause 20. The user interface of any of clauses 18 to 19, further comprising at least one adjacent region that displays brain scan data temporally contiguous with the brain imaging data in the window.

Clause 21. The user interface of any of clauses 18 to 20, further comprising a user interface element actuable by the technician that, when actuated, causes a machine learning model for ranking windows of brain imaging data based on likelihood of showing an epileptiform discharge to update based on feedback provided by the technician in the feedback region.

Clause 22. The user interface of any of clauses 18 to 21, further comprising a rendering of a brain with an indication of a location in the brain of an onset region of epileptic seizure, the location updated in response to feedback provided by the technician in the feedback region.

Clause 23. The user interface of clause 22, wherein a visual appearance of the indication of the location in the brain of the onset region of the epileptic seizure changes based on a confidence level determined from feedback provided by the technician in the feedback region.

Conclusion

While certain example embodiments have been described, including the best mode known to the inventors for carrying out the invention, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions and changes in the form of the methods and systems described herein may be made without departing from the spirit of the inventions disclosed herein. Skilled artisans will know how to employ such variations as appropriate, and the embodiments disclosed herein may be practiced otherwise than specifically described. The accompanying claims and their equivalents are intended to cover such forms or modifications as would fall within the scope and spirit of certain of the inventions disclosed herein.

The terms "a," "an," "the" and similar referents used in the context of describing the invention are to be construed to cover both the singular and the plural unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context. The terms "portion," "part," or similar referents are to be construed as meaning at least a portion or part of the whole including up to the entire noun referenced.

It should be appreciated that any reference to "first," "second," etc. elements within the Summary and/or Detailed Description is not intended to and should not be construed to necessarily correspond to any reference of "first," "second," etc. elements of the claims. Rather, any use of "first" and "second" within the Summary, Detailed Description, and/or claims may be used to distinguish between two different instances of the same element (e.g., two different sensors).

In closing, although the various configurations have been described in language specific to structural features and/or methodological acts, it is to be understood that the subject matter defined in the appended representations is not necessarily limited to the specific features or acts described. Rather, the specific features and acts are disclosed as example forms of implementing the claimed subject matter.

Furthermore, references have been made to publications, patents and/or patent applications throughout this specification. Each of the cited references is individually incorporated herein by reference for its particular cited teachings as well as for all that it discloses.

The invention claimed is:

1. A method of identifying epileptiform discharges in brain scan data comprising:

a) receiving the brain scan data;

b) segmenting the brain scan data into a plurality of windows;

c) extracting one or more features from the plurality of windows;

d) identifying, by a machine learning model, based on the one or more features a first window from the plurality of windows that is most likely to show an epileptiform discharge;

e) presenting the first window to a technician;

f) receiving feedback from the technician on a likelihood that the first window shows an epileptiform discharge;

g) updating the machine learning model based on the feedback from the technician to create a modified machine learning model; and h) identifying, by the modified machine learning model, a second window from the plurality of windows that is most likely to show an epileptiform discharge.

2. The method of claim 1, wherein the brain scan data is generated by one of functional magnetic resonance imaging (fMRI), electroencephalography (EEG), magnetoencephalography (MEG), or intracranial electroencephalography (iEEG).

3. The method of claim 1, wherein extracting one or more features from the plurality of windows is based on one or more statistical features of the brain scan data.

4. The method of claim 3, wherein the one or more statistical features are average band power, mean, variance, skewness, or kurtosis.

5. The method of claim 1, wherein extracting one or more features from the plurality of windows is performed by generating a connected graph from the brain scan data and then generating a feature vector from the connected graph.

6. The method of claim 1, wherein identifying the first window from the plurality of windows that is most likely to show an epileptiform discharge comprises creating a ranked list of the windows based on the one or more features and identifying a highest-ranked window.

7. The method of claim 1, wherein updating the machine learning model comprises updating feature weights applied to the one or more features from the plurality of windows.

8. The method of claim 1, wherein updating the machine learning model comprises modifying a learning to rank algorithm used to rank the plurality of windows with an online learning technique that uses the feedback from the technician as a label for supervised training.

9. The method of claim 1, further comprising repeating steps e)-h) until an indication is received from the technician that a location of an onset region of epileptic seizure in a brain can be identified.

10. The method of claim 9, further comprising updating at least one of a patient-specific machine learning model or a global model based on the feedback from the technician, wherein the patient-specific machine learning model or the global model is used as the machine learning model for initially identifying a window that is most likely to show an epileptiform discharge in a subsequent evaluation of different brain scan data.

11. The method of claim 1, further comprising generating a visualization of a brain showing a predicted location for an onset region of epileptic seizure based on epileptiform discharges identified by the technician.

12. A system for identifying epileptiform discharges in brain scan data comprising:

a processor; and computer-readable media communicatively connected to the processor;

a segmentation module, stored in the computer-readable media and comprising computer-executable instructions implemented by the processor, configured to segment brain scan data into a plurality of windows;

a featurizer, stored in the computer-readable media and comprising computer-executable instructions implemented by the processor, configured to extract one or more features from the plurality of windows;

a machine learning model, stored in the computer-readable media and comprising computer-executable instructions implemented by the processor, configured to identify a first window from the plurality of windows that is most likely to show an epileptiform discharge based on the one or more features; and a display device, connected to the processor, configured to present the first window to a technician together with one or more user interface elements actuable by the technician to indicate a likelihood that the first window shows an epileptiform discharge.

13. The system of claim 12, further comprising an online learning module, stored in the computer-readable media and comprising computer-executable instructions implemented by the processor, configured to update the machine learning model based on feedback provided by the technician interacting with the one or more user interface elements.

14. The system of claim 12, further comprising one or more sensors configured to detect brain activity and generate the brain scan data.

15. The system of claim 12, further comprising a model selection module, stored in the computer-readable media and comprising computer-executable instructions implemented by the processor, configured to select the machine learning model from multiple pre-existing machine learning models or to create an ensemble model from the multiple pre-existing machine learning models.

16. A system comprising:

a processor configured to implement a machine learning model, wherein the machine learning model identifies a window of brain scan data as most likely to show an epileptiform discharge based on one or more features extracted from a plurality of windows; and a user interface for identifying epileptiform discharges in brain scan data comprising: a main region that displays the window of brain scan data; and a feedback region that displays one or more user interface elements actuable by a technician to indicate a likelihood that the window of brain scan data in the main region shows an epileptiform discharge.

17. The user interface system of claim 16, wherein the one or more user interface elements of the feedback region are further configured to, upon actuation, cause the processor to replace the window of brain scan data in the main region with a different window of brain scan data that is not temporally contiguous and is identified by the machine learning model as next most likely to show an epileptiform discharge.

18. The user interface system of claim 16, further comprising a user interface element actuable by the technician that is configured to, when actuated, causes a cause the machine learning model for ranking windows of brain imaging data based on likelihood of showing an epileptiform discharge to update based on feedback provided by the technician in the feedback region.

19. The user interface system of claim 16, further comprising wherein the user interface displays a rendering of a brain with an indication of a location in the brain of an onset region of epileptic seizure, wherein the location rendering is updated by the processor in response to feedback provided by the technician in the feedback region.

20. The user interface system of claim 19, wherein the user interface displays a change to a visual appearance of the indication of the location in the brain of the onset region of the epileptic seizure changes, the change based on a confidence level determined by the processor from feedback provided by the technician in the feedback region.

* * * * *